United States Patent
Crisco

(10) Patent No.: US 7,503,211 B2
(45) Date of Patent: Mar. 17, 2009

(54) DRIVEN MUSCULOSKELETAL JOINT TESTING

(75) Inventor: Joseph J. Crisco, Barrington, RI (US)

(73) Assignee: Rhode Island Hospital, Providence, RI (US)

( * ) Notice: Subject to any disclaimer, the term of this patent is extended or adjusted under 35 U.S.C. 154(b) by 105 days.

(21) Appl. No.: 11/267,840

(22) Filed: Nov. 4, 2005

(65) Prior Publication Data

US 2006/0162444 A1    Jul. 27, 2006

Related U.S. Application Data

(60) Provisional application No. 60/625,190, filed on Nov. 5, 2004.

(51) Int. Cl.
*A61B 5/22* (2006.01)
(52) U.S. Cl. ................................... 73/379.01
(58) Field of Classification Search ............. 73/379.01, 73/379.02; 600/592; 601/5; 128/774
See application file for complete search history.

(56) References Cited

U.S. PATENT DOCUMENTS

| | | | | |
|---|---|---|---|---|
| 4,231,255 A | * | 11/1980 | Haski et al. ............. | 73/379.02 |
| 4,732,379 A | * | 3/1988 | Bodine-Reese et al. ..... | 482/134 |
| 5,078,152 A | * | 1/1992 | Bond et al. .................. | 600/587 |
| 5,178,152 A | * | 1/1993 | Ozawa ........................ | 600/493 |
| 5,303,715 A | * | 4/1994 | Nashner et al. .............. | 600/595 |
| 5,558,627 A | * | 9/1996 | Singer et al. .................. | 602/13 |
| 6,016,607 A | | 1/2000 | Morimoto et al. ............ | 33/1 M |
| 6,676,669 B2 | | 1/2004 | Charles et al. ............... | 606/130 |
| 6,723,106 B1 | | 4/2004 | Charles et al. ............... | 606/130 |
| 6,878,122 B2 | * | 4/2005 | Cordo ............................ | 601/5 |
| 2004/0143415 A1 | | 7/2004 | Jay ............................. | 702/150 |

FOREIGN PATENT DOCUMENTS

DE    36 36 843 A1    5/1987
WO    WO 88/04536    6/1988

OTHER PUBLICATIONS

Barnett et al., "Muscle tension and joint mobility", *Ann. Rheum. Dis.*, 28:652-654 (1969).
Charnley et al., "The lubrication of animal joints", *Symposium on Biomechanics.*, pp. 12-19 (1959).
Linn et al., "The lubrication of animal joints - the arthrotripsometer", *J. Bone Joint Surg.*, 49A(6):1079-1097 (1967).
Linn, F.C., "Lubrication of animal joints - the mechanism", *J. Biomechanics*, 1:193-205 (1968).
Unsworth et al., "The frictional behavior of human synovial joints - Part I: natural joints", *J. Lubrication Technol.*, pp. 369-376 (1975).
Unsworth et al., "Some new evidence on human joint lubrication", *Annals Rheum. Dis.*, 34:277-285 (1975).

* cited by examiner

*Primary Examiner*—Jewel V Thompson
(74) *Attorney, Agent, or Firm*—Ingrid A. Beattie; Mintz, Levin, Cohn, Ferris, Glovsky and Popeo, P.C.

(57) ABSTRACT

An apparatus for testing natural, partially artificial, or artificial musculoskeletal joints is provided as well as a method for using the same. In one aspect, the system employs a weighted, articulated apparatus, such as a pendulum, moving in response to a driving signal to determine a property of the musculoskeletal joint. Also within the invention is a method of growing cells under physiologic conditions of a musculoskeletal joint.

21 Claims, 4 Drawing Sheets

DRIVEN MUSCULOSKELETAL JOINT TESTING

CROSS-REFERENCE TO RELATED ACTIONS

This application claims the benefit of U.S. Provisional Application No. 60/625,190 filed Nov. 5, 2004.

BACKGROUND

Musculoskeletal joints include bones that move relative to one another. The motion of the bones is facilitated by lubricating synovial fluid that lies in a space (intra-articular space) between the moving bones in the joint. In living beings, the body produces the synovial fluid to ease the effort of moving the joints, and to reduce wear on the contact points of the moving bones.

Similar principles apply to the motion of living natural joints, artificial joints, or partially artificial joints. Artificial and partially artificial joints include one or more elements made of synthetic, artificial materials. An artificial lubricating fluid, or a wear-resistant smooth material can be used to make or coat the artificial portions of the artificial or partially artificial joints.

Testing and measurement of various physiological and mechanical properties of a musculoskeletal joint can be carried out by observing its response to predetermined conditions. For example, certain mechanical properties of a musculoskeletal joint can be tested by subjecting the joint to a force and observing the dynamic response of the joint to the applied force.

Experiments have been conducted on musculoskeletal joints to determine the coefficients of friction between parts of the joints that move relative to one another. Earlier works studied the lubrication of animal joints in the context of arthritis and rheumatism research using a pendulum connected to a portion of the joint. Some of these experiments involved attaching a pendulum to one portion of a musculoskeletal joint, fixing another portion of the joint, then observing the system's response when the pendulum is swung under the force of gravity. Properties of the joint could be deduced using the principles of mechanics to measure the frictional coefficients of the musculoskeletal joint for example.

SUMMARY

The invention features a device and system to test joints, e.g., mammalian joints or prosthetic artificial joints, and to culture cells or tissue explants under physiologic conditions of a natural articulating joint. For example, the device is useful for fatigue testing of natural, artificial, or bioprosthetic joints. The apparatus is also used to culture and test cells, tissues or tissue replacements, under physiologic stress conditions.

An exemplary embodiment of the invention is directed to an apparatus for testing at least one of a natural, artificial, or partially artificial musculoskeletal joint, the apparatus including a weight attached to a first portion of the joint; and a driver configured to attach to a second portion of the joint and to support the second portion with the weight forcing the first portion toward the second portion of the joint, the driver having at least one degree of freedom in which the driver may move the first portion of the joint; wherein the weight is configured to provide an indication of motion of the first portion of the joint associated with a characteristic of the musculoskeletal joint.

Another exemplary embodiment is directed to a method for testing at least one of a natural, artificial, or partially-artificial musculoskeletal joint including first and second portions that can at least one of pivot and rotate relative to each other, the method including: attaching a weight to the first portion of the joint; arranging the joint such that the first portion is above the second portion; moving the second portion of the joint in at least one direction to induce movement of the first portion of the joint relative to the second portion of the joint; and measuring the induced motion of the first portion of the joint in response to movement of the first portion of the joint.

Yet another exemplary embodiment is directed to a system for measuring a mechanical property of a joint, the system comprising in combination, a driving means for driving a first portion of the joint in at least one dimension; a pendulum attached to a second portion of the joint, the second portion of the joint being movable relative to the first portion; and a detector disposed and configured to detect motion of the pendulum.

Other features and advantages of the invention will be apparent from the following description of the preferred embodiments thereof, and from the claims

DETAILED DESCRIPTION

Various aspects of the invention permit testing and examination of a musculoskeletal joint through driving at least one portion of the joint and observation of a response of the joint system to the driving. For example, a weighted articulated apparatus is attached to one portion of the musculoskeletal joint while another portion of the musculoskeletal joint is driven with some predetermined driving force. The driven portion of the musculoskeletal joint can be controllably translated, moved, or accelerated. In such a driven system, the weighted articulated apparatus responds to the drive in a manner consistent with both the driving dynamics (force, impulse, translation, velocity, acceleration, etc.) and the mechanical properties of the musculoskeletal joint. That is, the response of the weighted articulated apparatus will depend on the applied drive and will also depend on the mechanical and dynamical properties of the musculoskeletal joint. Therefore, if the driving forces are known, and the response of the weighted articulated apparatus are measured (and hence known), it is possible to determine something about the character of the musculoskeletal joint itself. Other embodiments are within the scope of the invention.

Figure 1:
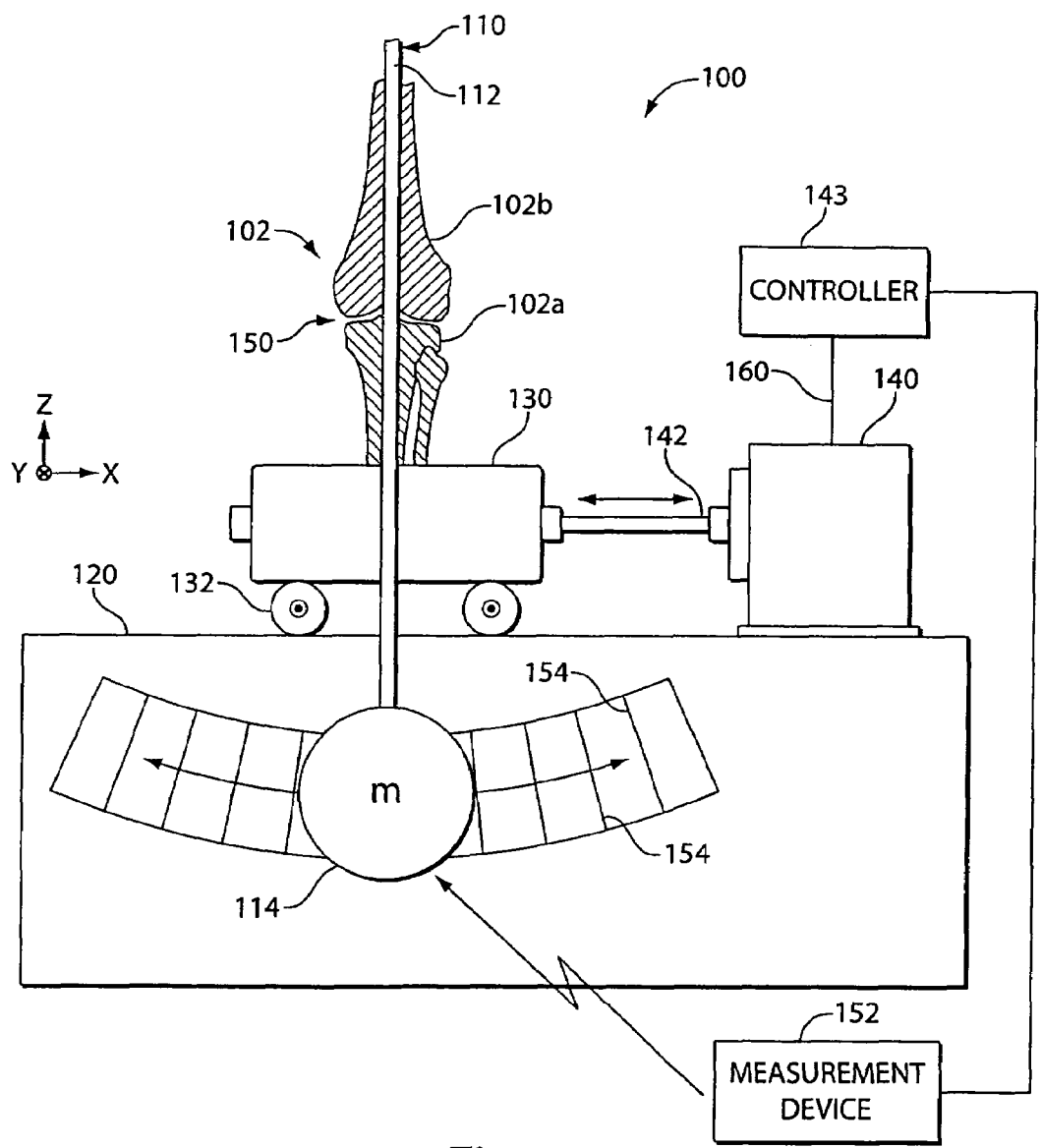
FIG. 1 is a side view of a musculoskeletal joint testing system in accordance with the invention.

Consider a first example of such a driven musculoskeletal joint testing system 100, illustrated in FIG. 1. The system 100 includes a musculoskeletal joint 102 to be tested with respect to a mechanical or other property thereof. The musculoskeletal joint 102 includes two bone portions: a first bone portion 102a that is fixed with respect to a support base 130, and a second bone portion 102b which can move relative to the first fixed portion 102a and base 130. The "bone" portions 102a, 102b may be made of natural bone or artificial materials.

The base 130 rests on a reference (stationary) platform 120 that is substantially larger and heavier than any of the other components of system 100, so that the platform 120 does not move appreciably when any of the components of the system are moved. Alternatively, the base 130 could be placed on the floor, the ground, or any other stationary surface. The base 130 is equipped with wheels 132 (although rollers, bearings, or other devices may be used) to permit the base 130 to roll, rotate, oscillate, translate, or otherwise move with respect to the platform 120.

A driver motor or other driver actuator 140 is mounted to the platform 120 and configured to provide a driving motion or force to the base 130, and hence to the first musculoskeletal joint portion 102a. The driver actuator 140 is, e.g., a linear translator configured to provide a periodic force to the left and to the right as indicated by a double-ended arrow 141. The driver apparatus 140 may also provide non-periodic driving responses depending on the nature of the test being performed. The driver actuator 140 provides a controllable driving input to the base 130, and may be controlled by a controller 143 (e.g., a processor and software code) that sends electrical or electromechanical signals to control the action of the driver actuator 140. The base 130 and driver actuator 140 are coupled by a coupling or connector 142, which may be rigid or otherwise drive base 130 through tension or compression.

While the actuator 140 is a linear actuator, the range of motion of the base 130, being controlled by one or more driver actuators is not limited to linear (back and forth) or periodic motion. Indeed, various forms of motion in more than one degree of freedom may be provided. For example, one or more actuators could be connected to the base 130 to induce planar (x-y) motion and/or rotational motion, e.g., about the z-axis.

A weighted articulated apparatus, here a pendulum, 110 is connected to the second portion 102b of the musculoskeletal joint 102. The pendulum 110 includes an arm 112, having a length (L), and a weight 114 of a mass (m). This pendulum configuration is a driven pendulum, with the pendulum 110 being affected by a driving condition from the actuator 140. The length (L) and the mass (m) (including the mass of the arm 112) of the pendulum 110 can be adjusted or changed by physically changing the actual arm 112 or the weight 114 used, or by adjusting a setting or location of the arm 112 and/or the weight 114. Graduations 154 or other indicia of the movement of the pendulum 110 can be incorporated into the system 100 so that the response of the pendulum 110 to the actuator's induced motion may be monitored by a measurement device 152. The device 152 may be, e.g., an indicia can include external analog or digital imaging (camera) apparatus mounted to record the position, speed, angular position, acceleration, etc. of the pendulum 110.

The first and second portions of musculoskeletal joint 102 substantially make contact at a vertex portion 150. The vertex portion 150 may be shaped in one of many configurations depending on the nature of the musculoskeletal joint 102 being tested. For example, the vertex portion 150 may resemble a ball and socket joint, the ball portion (e.g. 102b) riding in the socket portion (e.g. 102a) of the musculoskeletal joint 102.

A fluid may be placed in the vertex region 150 so that friction between the first and second portions 102a, 102b of the joint 102 is reduced. Lubricating fluids between the moving portions of the joint 102 can form a layer that helps prevent the portions 102a and 102b from actually physically touching one another. Therefore, the portion 102b may "float" on the portion 102a of the joint 102.

Figure 2:
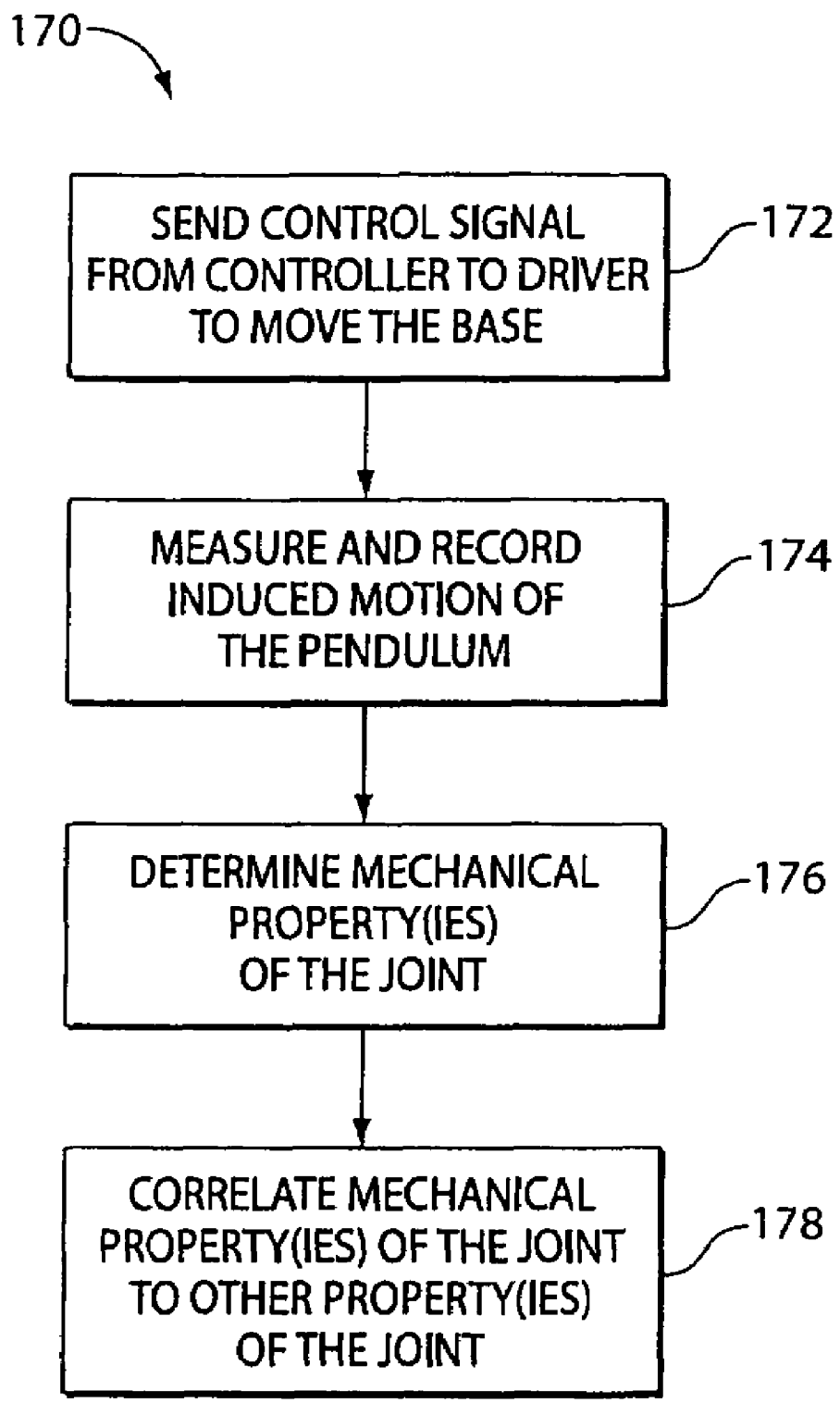
FIG. 2 is a block flow diagram of a process of testing a joint using the system shown in FIG. 1.

In operation, referring to FIG. 2, with further reference to FIG. 1, a process 170 for testing the joint 102 using the system 100 includes the stages shown. The process 170, however, is exemplary only and not limiting. The process 160 may be altered, e.g., by having stages added, removed, or rearranged.

At stage 172, a control signal is delivered through a control line 160 from the controller 143 to the driver actuator 140 to cause actuation or movement of the arm or linkage 142 to move base 130. The movement of the base 130 causes the first portion 102a of the joint 102 to move. The movement of the driven base 130 and the portion 102a is transmitted through the vertex portion 150 (which may contain fluid) to the second portion 102a of the joint 102.

At stage 174, the pendulum 110 moves (responds) with some response consistent with a force balance experienced by the pendulum 110 at any point in time, and the motion of the pendulum 110 or any selected portion or point thereof is observed, measured, or recorded. The portions 102a, 102b move (e.g., pivot, translate, and/or slide) relative to each other. The movement induced in the pendulum 110 is preferably measured and recorded by the measurement device 152 (e.g., in conjunction with the graduations 154).

At stage 176, one or more mechanical properties of the joint 102 or the fluid in the vertex 150 are determined from the response of the pendulum 110 to the movement of the driven base 130. The controller 143 processes data from the measurement device 152 and data regarding the driving of the base 130 to determine one or more desired characteristics, e.g., friction of the joint 102.

At stage 178, the mechanical properties and responses of system 100 can be correlated or related to other properties of the joint 102. For example, one or more physiological properties, biological properties, chemical properties, etc. of the joint 102 or a synovial fluid may be determined directly or indirectly from the response of the dynamic pendulum 110.

The controller 143 includes software computer code instructions for causing a computer processor to perform functions, the code including algorithms for controlling the motion of the base 130 through the actuator 140. Specifically, a feedback system can be used in conjunction with the other components of system 100 to provide the proper driving dynamics for the system and/or in response to the motion of the weighted articulated apparatus (pendulum) 110. Data, regarding motion of the pendulum 110, from the measurement device 152 are provided to the controller 143. The controller 143 processes these data to regulate further motion of the pendulum 110 via the base 130 by providing appropriate commands to the driver 140.

Because only the one portion 102a of the joint 102 is driven by the driver actuator 140, the driver actuator 140 does not require much power to operate, and can be smaller and cheaper than current commercial load and fatigue testers used in testing natural and artificial musculoskeletal joints. Load sensors could be coupled to one or more parts of system 100 to provide additional information that can be used by the controller 143.

Using embodiments of the invention, mechanical properties and properties correlating to the mechanics of musculoskeletal joints can be investigated, measured, and tested using the driven system 100. Dynamic sensing and feedback capabilities can be included to provide an indication of the properties of the musculoskeletal joint 102 and to diagnose or assist in development of artificial joints. The system 100 may be used with a variety of joints, e.g., knee and hip joints. Fatigue testing and performance tests can benefit from the use of the invention and exemplary embodiments provided herein. Also, improved understanding of the dynamics of natural, artificial and partially artificial joints is possible using the invention.

Figure 3:
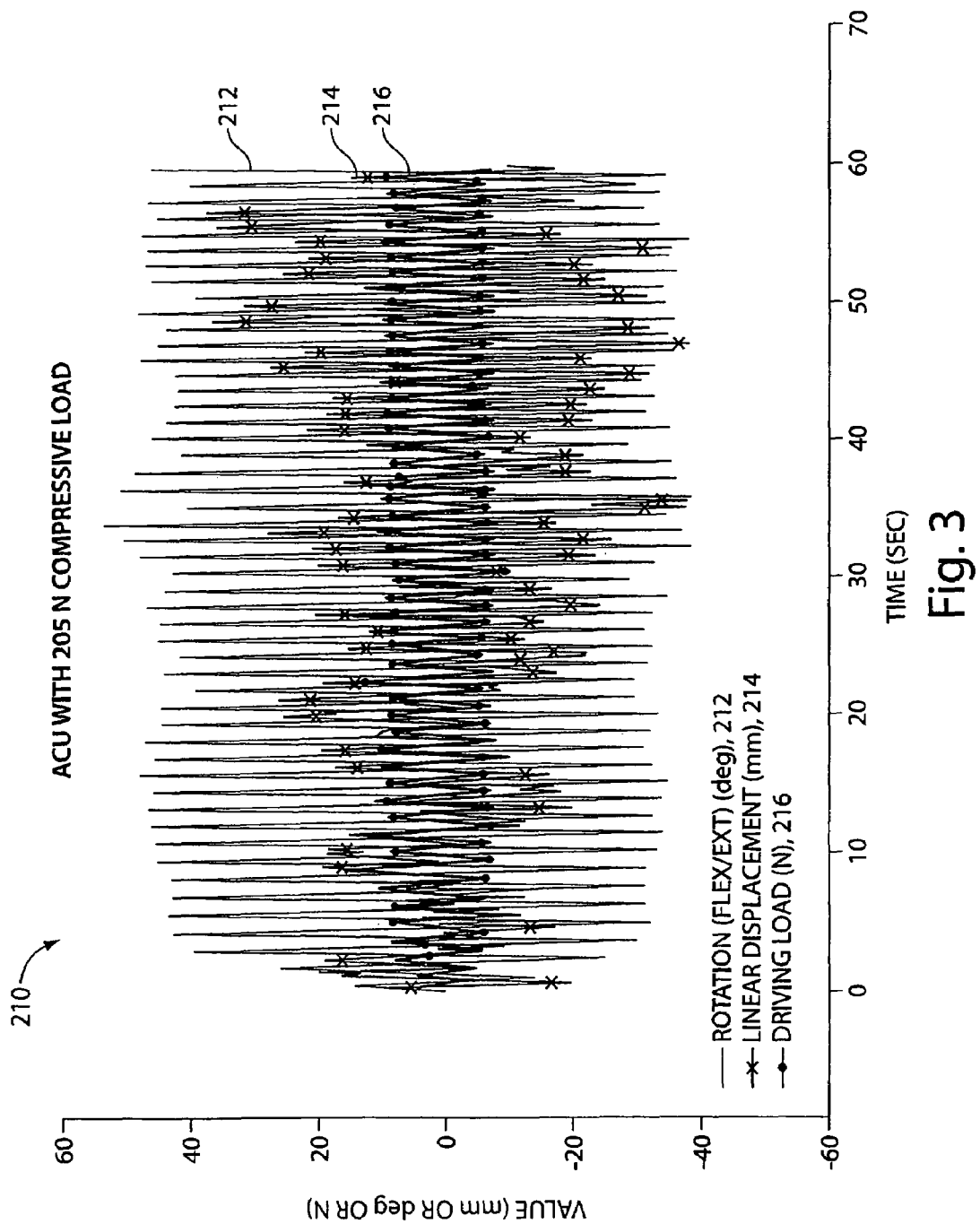
FIG. 3 is a graph of joint rotation, linear displacement, and driving load for an experiment conducted using the system shown in FIG. 1.

Referring to FIG. 3, a graph 210 shows experimental data for a test using a musculoskeletal joint testing system 100. The test data shown in the graph 210 are from a one minute portion of a test. A plot 212 illustrates the rotation of the pendulum 112 in degrees. Here, the pendulum 112 swung through a rotation between about +52° and about −40°. A plot 214 illustrates a linear displacement in mm of the base 130. Here, the base 130 moved between about +40 mm and about −40 mm. A plot 216 illustrates a driving load in Newtons provided by the mass 114. Here, the driving load ranged from about +10 N to about −10 N. The mass 114 itself induced about a 205 N compressive load on the joint 102.

Figure 4:
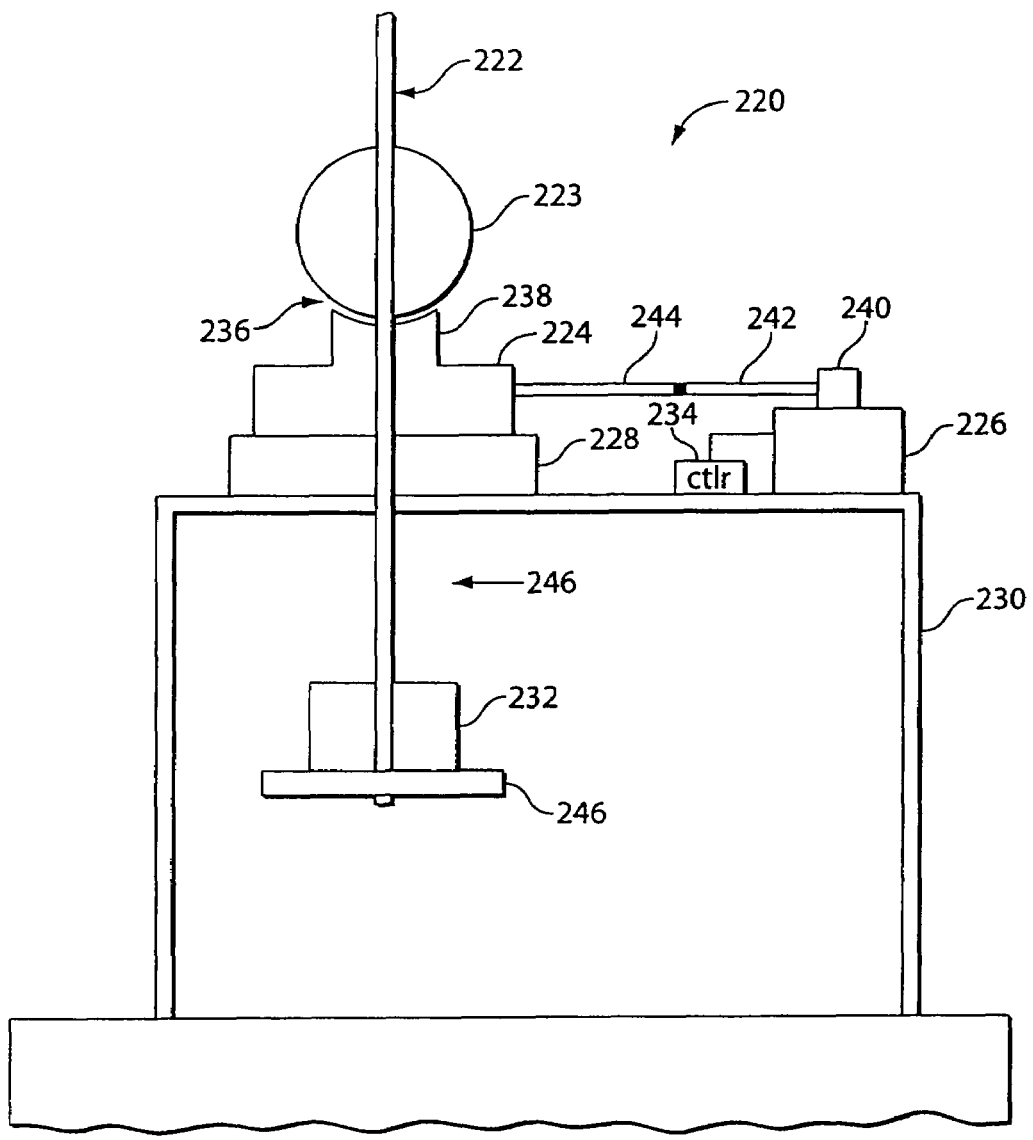
FIG. 4 is a side view of an exemplary musculoskeletal joint testing system in accordance with the invention.

Referring to FIG. 4, a driven musculoskeletal joint testing system 220 includes a pendulum 222, an upper artificial joint portion 223, a base 224, an actuator 226, a linear bearing 228, a table 230, a mass 232, and a controller 234. The system 220 may be used, e.g., to test cells inserted in a space 236 between the upper artificial joint portion 223 and a lower artificial joint portion 238, that in this embodiment is part of the base 224. A housing (not shown) can be placed around the base and upper joint portion 223, e.g., to protect against environmental contamination of the cells under test. The base 224 is connected to the actuator motor 226, that includes a wheel 240 pivotably connected to a rod 242. The wheel 240 is configured to, and the motor 226 is configured to cause the wheel to, oscillate. The oscillation causes linear and rotation motion of the rod 242, that is pivotably connected to a linkage 244 that is connected to the base 224 such that the linkage 244 moves in a linear, back and forth, manner under control of the controller 234. The base 224 and the linear bearing 228 are configured such that the base 224 can move linearly relative to the linear bearing 228, which is fixed relative to the table 230. The pendulum 222 is attached to the upper joint portion 222 that, in conjunction with the lower joint portion 238, simulates a desired joint. The upper and lower joint portions 223, 238 may be, e.g., plastic. The pendulum 222 is generally U-shaped when viewed along line 246 to attach to either side of the upper joint portion 223 and to extend under the table 230. The pendulum 222 includes a platform 246 to support the mass 232.

Tissue Culture Under Physiological Conditions

The system 100 or the system 220 can be used to grow and test the performance of musculoskeletal tissues and cells. For example, cartilage cells are propagated by providing a piece of articular cartilage from a healthy section of the knee, isolating chondrocytes, and expanding the number of chondrocytes in culture for subsequent implantation of the cells into the joint of the donor or a histocompatible recipient. Earlier methods, such as those in which cartilage cells are grown on an elastic membrane, have certain drawbacks including inconsistent growth and differentiation depending on the position the cell(s) occupy on the elastic membrane to which a tension (i.e., stretching, vacuum, or air blast force) is applied. Drawbacks of earlier methods include reduced biomechanical strength and reduced growth compared to normal cartilage cells. The present apparatus exerts physiological loads that simulate mechanical stresses encountered by cells in joints or other biomechanically active environments.

The driven pendulum system applies both dynamic compression and shear loading to an intra-articular space/interface of a joint. This loading is similar to that applied to articular cartilage in a natural articular joint during daily activity. Cells, e.g., isolated chondrocytes, fibroblast, osteoblasts, osteoclasts, stem cells, or tissue explants are grown and differentiated under compressive load and shear load conditions that simulate the physiologic conditions. The advantage of this system is that it applies both dynamic compression and shear forces, whereas earlier systems applied only tension. The combination of compressive and shear forces in physiologic ranges promotes mechanical and cellular changes that induce appropriate growth and differentiation of cells for physiologic testing and/or transplantation for tissue re-engineering purposes. Cells grown in the apparatus described herein are characterized by enhanced proliferation (10%, 25%, 50%, 100%, 2-fold, 5-fold, 10-fold or more) and differentiation (e.g., morphology, elaboration of growth factors (10%, 25%, 50%, 100%, 2-fold, 5-fold, 10-fold or more)) compared to cells grown under static growth conditions (or under conditions in which only a single force is applied, e.g., culture on a deformable or elastic membrane subjected to oscillating or intermittent pressure).

Primary or immortalized cells such as cartilage cells are cultured under sterile conditions at the vertex portion 150 of the apparatus. Vertex portion 150, musculosketal joint portion 102 (including 102a and 102b) are optionally encased in a sterile cell culture chamber. The chamber may be heated and humified. Alternatively, the entire apparatus is placed in an incubator or warm room depending on the cells or tissue being tested and the desired loads. Cell culture conditions in the chamber or incubator are typically 37° C. and 5-10% $CO_2$.

The dynamic forces exerted at the vertex portion 150 simulate those experienced within an intra-articular joint, e.g., a knee, elbow, hip, shoulder joint, of a mammal. Compressive load corresponds to body weight of the subject, e.g., a human being, or a fraction thereof (e.g., 10%, 20%, 50%, 75%, 100%, 200%, 300% or more of body weight). For example, the compressive force is 33 Newtons/kilogram (N/kg) of body mass, which corresponds to approximately 3.3× body weight of an average adult human subject. Accordingly, the compressive force exerted at vertex portion 150 is 10, 50, 100, 200, 300 N. Shear force is simultaneously or sequentially exerted at vertex portion 150. Physiologically relevant shear forces can be applied at the rate in the range of a few (1-5) cycles per second as in the range of walking, or faster (5-10 or more cycles) in the testing of artificial joints in order to more quickly examine wear properties.

In preferred embodiments, the cells are grown in a 3-dimensional (3-d) culture system. The cell culture unit is a soft or hard tissue, a biomaterial, a deformable material, bio-artificial material or viscoelastic material. Cell culture units include a bio-artificial tendon construct or cartilaginous (or bio-engineered cartilage) construct. For example, the cells are dispersed or embedded in a 3-d scaffold or structure, e.g., a collagen sponge, a collagen-coated cellulose sponge, a chitosan matrix, a chitosan/collagen matrix, a calcium phosphate scaffold, a hydrogel matrix, a synthetic peptide hydrogel matrix, a woven or non-woven silk scaffold, or a woven or non-woven synthetic polymeric structure. The scaffold is a membrane, sponge, or foam. In embodiments in which the scaffold is a membrane or other 2-dimensional structure, the membrane is not subjected to a tension (stretching or gripping) force, a vacuum force or exposure to a blast of compressed air.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations. Further, while the description above refers to the invention, the description may include more than one invention.

What is claimed is:

1. An apparatus for testing at least one of a natural, artificial, or partially artificial musculoskeletal joint, the apparatus comprising:
   a weight attached to a first portion of the joint; and
   a driver configured to attach to a second portion of the joint and to support the second portion with the weight forcing the first portion toward the second portion of the joint, the driver having at least one degree of freedom in which the driver may move the first portion of the joint;
   wherein the weight is configured to provide an indication of motion of the first portion of the joint associated with a characteristic of the musculoskeletal joint.

2. The apparatus of claim 1, wherein the driver comprises a moveable base configured to connect to and support the second portion of the joint.

3. The apparatus of claim 2, wherein the driver further comprises an actuator that is connected to the moveable base and that is configured to induce movement of the moveable base along the at least one degree of freedom.

4. The apparatus of claim 1, wherein the driver is configured to move the second portion of the joint in an oscillatory manner.

5. The apparatus of claim 1, wherein the driver is configured to move the second portion of the joint in at least two dimensions.

6. The apparatus of claim 1, wherein the driver is configured to rotate the second portion of the joint.

7. The apparatus of claim 1, wherein the weight is a pendulum.

8. The apparatus of claim 1, further comprising a sensor configured to sense at least one of acceleration, a velocity, and a displacement of the pendulum.

9. The apparatus of claim 8, further comprising a processor coupled to the sensor and the driver and configured to use information from the sensor and the driver to determine and indication of a mechanical resistance in the musculoskeletal joint.

10. The apparatus of claim 8, further comprising a controller coupled to the sensor and the driver and configured to use information regarding motion of the pendulum to control the motion of said driver.

11. A method for testing at least one of a natural, artificial, or partially-artificial musculoskeletal joint including first and second portions that can at least one of pivot and rotate relative to each other, the method comprising:
    attaching a weight to the first portion of the joint;
    arranging the joint such that the first portion is above the second portion;
    moving the second portion of the joint in at least one direction to induce movement of the first portion of the joint relative to the second portion of the joint; and
    measuring the induced motion of the first portion of the joint in response to movement of the first portion of the joint.

12. The method of claim 11, further comprising determining a characteristic of the joint from first information obtained from measuring the induced motion of the first portion of the joint and second information associated with moving the second portion of the joint.

13. The method of claim 12, wherein the characteristic is friction in the joint and the first information includes displacement of the weight.

14. The method of claim 11, wherein moving the second portion of the joint comprises causing the second portion to oscillate along at least one axis of motion.

15. The method of claim 11, wherein moving the second portion of the joint includes moving the second portion in at least two dimensions.

16. The method of 15, wherein moving the second portion of the joint includes rotating the second portion of the joint.

17. The method of 11, wherein moving the second portion of the joint includes rotating the second portion of the joint.

18. The method of claim 11, wherein the weight comprises a pendulum and measuring the induced motion comprises detecting movement of the pendulum attached to the first portion of the musculoskeletal joint in response to movement of the second portion of the joint.

19. A system for measuring a mechanical property of a joint, the system comprising in combination:
    driving means for driving a first portion of the joint in at least one dimension;
    a pendulum attached to a second portion of the joint, the second portion of the joint being movable relative to the first portion; and
    a detector disposed and configured to detect motion of the pendulum.

20. The system of claim 19, further comprising a controller electrically coupled to the detector and the driving means and configured to control the driving of the first portion of the joint.

21. The system of claim 19 wherein the controller is further configured to determine a characteristic of the joint using information regarding the driving of the first portion of the joint and information regarding motion of the pendulum detected by the detector.

* * * * *